US00RE46208E

(19) United States
(12) Reissued Patent
Baranov et al.

(10) Patent Number: US RE46,208 E
(45) Date of Reissued Patent: *Nov. 22, 2016

(54) METHOD FOR CRYOGENICALLY TREATING TISSUE BELOW THE SKIN SURFACE

(75) Inventors: Eugene Baranov, San Diego, CA (US); Nikolai I. Tankovich, San Diego, CA (US)

(73) Assignee: RELIANT TECHNOLOGIES, LLC, Hayward, CA (US)

( * ) Notice: This patent is subject to a terminal disclaimer.

(21) Appl. No.: 13/165,181

(22) Filed: Jun. 21, 2011

Related U.S. Patent Documents

Reissue of:

(64) Patent No.: 6,632,219
Issued: Oct. 14, 2003
Appl. No.: 09/523,225
Filed: Mar. 10, 2000

U.S. Applications:

(63) Continuation of application No. 11/250,139, filed on Oct. 13, 2005, now Pat. No. Re. 42,594, which is an application for the reissue of Pat. No. 6,632,219, which is a continuation-in-part of application No. 09/174,065, filed on Oct. 16, 1998, now Pat. No. 6,059,820.

(51) Int. Cl.
*A61B 18/18* (2006.01)
*A61B 19/00* (2006.01)
(Continued)

(52) U.S. Cl.
CPC ..... *A61B 18/02* (2013.01); *A61B 18/04* (2013.01); *A61B 2018/0047* (2013.01);
(Continued)

(58) Field of Classification Search
CPC ..... A61B 18/18; A61B 18/20; A61B 2018/00452; A61B 2018/0047; A61B 18/02; A61B 18/04; A61B 2018/0231; A61B 2018/0237; A61B 2018/025; A61B 2018/0262; A61N 5/00; A61N 2005/002; A61N 2005/007; A61N 2005/0644
USPC ..... 606/3, 8–13, 20, 23–28; 607/88–91, 93, 607/96, 100, 108; 128/898
See application file for complete search history.

(56) References Cited

U.S. PATENT DOCUMENTS 3,622,743 A 11/1971 Muncheryan
4,122,853 A 10/1978 Smith (Continued)

FOREIGN PATENT DOCUMENTS

EP 0827219 A2 3/1998
EP 0827716 A2 3/1998

(Continued)

OTHER PUBLICATIONS

US 6,344,051, 02/2002, Dumoulin-White et al. (withdrawn)

(Continued)

*Primary Examiner* — Ahmed Farah
(74) *Attorney, Agent, or Firm* — Thompson Hine LLP

(57) ABSTRACT

A laser treatment device and process with controlled cooling. The device contains a cooling element with high heat conduction properties, which is transparent to the laser beam. A surface of the cooling element is held in contact with the tissue being treated while at least one other surface of the cooling element is cooled by the evaporation of a cryogenic fluid. The cooling is coordinated with the application of the laser beam so as to control the temperatures of all affected layers of tissues. In a preferred embodiment useful for removal of wrinkles and spider veins, the cooling element is a sapphire plate. A cryogenic spray cools the top surface of the plate and the bottom surface of the plate is in contact with the skin. In preferred embodiments the wavelength of the laser beam is chosen so that absorption in targeted tissue is low enough so that substantial absorption occurs throughout the targeted tissue. In a preferred embodiment for treating large spider veins with diameters in the range of 1.5 mm, Applicants use an Er:Glass laser with a wavelength of 1.54 microns.

39 Claims, 15 Drawing Sheets

(51) Int. Cl.

| | |
|---|---|
| ***A61B 18/02*** | (2006.01) |
| *A61B 18/04* | (2006.01) |
| *A61B 18/00* | (2006.01) |
| *A61N 5/00* | (2006.01) |
| *A61N 5/06* | (2006.01) |

(52) U.S. Cl.

CPC ..... *A61B 2018/00452* (2013.01); *A61B 2018/0231* (2013.01); *A61B 2018/0237* (2013.01); *A61N 2005/002* (2013.01); *A61N 2005/0644* (2013.01)

(56) References Cited

U.S. PATENT DOCUMENTS 4,573,465 A 3/1986 Sugiyama et al.
4,587,396 A 5/1986 Rubin
4,653,495 A 3/1987 Nanaumi
4,718,416 A 1/1988 Nanaumi
4,733,660 A 3/1988 Itzkan
4,775,361 A 10/1988 Jacques et al.
4,930,504 A 6/1990 Diamantopoulos et al.
4,976,709 A 12/1990 Sand
5,000,752 A 3/1991 Hoskin et al.
5,104,392 A 4/1992 Kittrell et al.
5,106,387 A 4/1992 Kittrell et al.
5,128,509 A 7/1992 Black et al.
5,178,617 A 1/1993 Kuizenga et al.
5,192,278 A 3/1993 Hayes et al.
5,282,797 A 2/1994 Chess
5,302,259 A 4/1994 Birngruber
5,312,395 A 5/1994 Tan et al.
5,312,396 A 5/1994 Feld et al.
5,336,217 A 8/1994 Buys et al.
5,339,347 A 8/1994 Slatkin et al.
5,344,418 A * 9/1994 Ghaffari ..... 606/9
5,360,447 A 11/1994 Koop
5,411,502 A 5/1995 Zair
5,421,337 A 6/1995 Richards-Kortum et al.
5,423,803 A 6/1995 Tankovich et al.
5,474,549 A 12/1995 Ortiz et al.
5,486,172 A 1/1996 Chess
5,531,740 A 7/1996 Black
5,546,214 A 8/1996 Black et al.
5,558,666 A 9/1996 Dewey et al.
5,582,752 A 12/1996 Zair
5,586,981 A 12/1996 Hu
5,595,568 A 1/1997 Anderson et al.
5,611,795 A 3/1997 Slatkine et al.
5,616,140 A 4/1997 Prescott
5,618,284 A 4/1997 Sand
5,618,285 A 4/1997 Zair
5,624,434 A 4/1997 Abergel et al.
5,624,435 A 4/1997 Furumoto et al.
5,628,744 A 5/1997 Coleman et al.
5,632,741 A 5/1997 Zavislan et al.
5,643,252 A 7/1997 Waner et al.
5,655,547 A 8/1997 Karni
5,713,364 A 2/1998 DeBaryshe et al.
5,733,278 A 3/1998 Slatkine et al.
5,735,844 A * 4/1998 Anderson et al. ..... 606/9
5,746,735 A 5/1998 Furumoto et al.
5,759,200 A 6/1998 Azar
5,798,498 A 8/1998 Zair
5,807,386 A 9/1998 Slatkine et al.
5,810,801 A 9/1998 Anderson et al.
5,814,040 A * 9/1998 Nelson et al. ..... 606/9
5,814,042 A 9/1998 Zair
5,817,089 A 10/1998 Tankovich et al.
5,820,626 A * 10/1998 Baumgardner ..... 606/13
5,830,208 A * 11/1998 Muller ..... 606/9
5,843,073 A 12/1998 Sinofsky
5,860,967 A 1/1999 Zavislan et al.
5,860,968 A 1/1999 Wojcik et al.
5,865,754 A 2/1999 Sevick-Muraca et al.
5,879,326 A 3/1999 Godshall et al.
5,879,346 A 3/1999 Waldman et al.
5,885,211 A 3/1999 Eppstein et al.
5,897,549 A 4/1999 Tankovich
5,906,609 A 5/1999 Assa et al.
5,908,415 A 6/1999 Sinofsky
5,925,035 A 7/1999 Tankovich
5,938,657 A 8/1999 Assa et al.
5,947,956 A 9/1999 Karell
5,957,915 A 9/1999 Trost
5,964,749 A 10/1999 Eckhouse et al.
5,968,033 A 10/1999 Fuller et al.
5,970,983 A 10/1999 Karni et al.
5,976,123 A 11/1999 Baumgardner et al.
5,980,512 A 11/1999 Silberg
5,983,900 A 11/1999 Clement et al.
5,984,915 A 11/1999 Loeb et al.
5,995,265 A 11/1999 Black et al.
5,995,866 A 11/1999 Lemelson
5,997,530 A 12/1999 Nelson et al.
6,015,404 A 1/2000 Altshuler et al.
6,022,316 A 2/2000 Eppstein et al.
6,027,496 A 2/2000 Loomis et al.
RE36,634 E 3/2000 Ghaffari
6,036,684 A 3/2000 Tankovich et al.
6,050,990 A 4/2000 Tankovich et al.
6,059,820 A * 5/2000 Baronov ..... 607/89
6,063,108 A 5/2000 Salansky et al.
6,074,384 A 6/2000 Brinkmann et al.
6,083,217 A 7/2000 Tankovich
6,096,029 A * 8/2000 O'Donnell, Jr. ..... 606/9
6,096,031 A 8/2000 Mitchell et al.
6,104,959 A * 8/2000 Spertell ..... 607/101
6,106,514 A 8/2000 O'Donnell, Jr.
RE36,872 E 9/2000 Zair
6,113,559 A 9/2000 Klopotek
6,120,497 A 9/2000 Anderson et al.
6,142,939 A 11/2000 Eppstein et al.
6,149,644 A 11/2000 Xie
6,149,645 A 11/2000 Tobinick
6,152,917 A 11/2000 Tankovich
6,162,211 A 12/2000 Tankovich et al.
6,165,170 A 12/2000 Wynne et al.
6,168,590 B1 1/2001 Neev
6,171,301 B1 1/2001 Nelson et al.
6,171,302 B1 1/2001 Talpalriu et al.
6,173,202 B1 1/2001 Eppstein
6,176,854 B1 1/2001 Cone
6,183,773 B1 2/2001 Anderson
6,197,020 B1 3/2001 O'Donnell, Jr.
6,219,575 B1 4/2001 Nemati
6,235,015 B1 5/2001 Mead, III et al.
6,241,753 B1 6/2001 Knowlton
6,245,060 B1 6/2001 Loomis et al.
6,248,103 B1 6/2001 Tannenbaum et al.
6,251,099 B1 6/2001 Kollias et al.
6,251,100 B1 6/2001 Flock et al.
6,264,649 B1 * 7/2001 Whitcroft et al. ..... 606/22
6,267,771 B1 7/2001 Tankovich et al.
6,273,884 B1 8/2001 Altshuler et al.
6,273,885 B1 8/2001 Koop et al.
6,315,772 B1 11/2001 Marchitto et al.
6,325,769 B1 12/2001 Klopotek
6,328,733 B1 12/2001 Trost
6,387,089 B1 5/2002 Kreindel et al.
6,406,474 B1 6/2002 Neuberger et al.
6,413,267 B1 7/2002 Dumoulin-White et al.
6,443,946 B2 9/2002 Clement et al.
6,443,978 B1 9/2002 Zharov
6,445,491 B2 9/2002 Sucha et al.
6,468,229 B1 10/2002 Grace et al.
6,475,138 B1 11/2002 Schechter et al.
6,508,813 B1 1/2003 Altshuler
6,514,278 B1 2/2003 Hibst et al.
6,517,532 B1 2/2003 Altshuler et al.
6,530,915 B1 3/2003 Eppstein et al.
6,537,270 B1 3/2003 Elbrecht et al.
6,572,637 B1 6/2003 Yamazaki et al.
6,575,963 B1 6/2003 Van Saarloos et al.
6,579,283 B1 6/2003 Tobinick

(56) References Cited

U.S. PATENT DOCUMENTS

| | | | |
|---|---|---|---|
| 6,605,080 | B1 | 8/2003 | Altshuler et al. |
| 6,607,523 | B1 | 8/2003 | Asah et al. |
| 6,632,219 | B1 | 10/2003 | Baranov et al. |
| 6,680,999 | B1 | 1/2004 | Garcia |
| 6,685,699 | B1 | 2/2004 | Eppstein et al. |
| 6,743,211 | B1 | 6/2004 | Prausnitz et al. |
| 6,758,845 | B1 | 7/2004 | Weckwerth et al. |
| 6,881,212 | B1 | 4/2005 | Clement et al. |
| 7,204,832 | B2 | 4/2007 | Altshuler et al. |

FOREIGN PATENT DOCUMENTS

| | | | |
|---|---|---|---|
| JP | 58086787 | A | 5/1983 |
| JP | 01191801 | A | 8/1989 |
| JP | 09285471 | A | 11/1997 |
| WO | 9824502 | A1 | 6/1998 |
| WO | 9824507 | A2 | 6/1998 |
| WO | 9824514 | A1 | 6/1998 |
| WO | 9927997 | A1 | 6/1999 |
| WO | 0139834 | A1 | 6/2001 |

OTHER PUBLICATIONS

Anderson, R.R. et. Al., "Laser-Tissue Interactions," Cosmetic Laser Surgery, 2000, pp. 1-30, Mosby.

McKenzie, A.L, "A Three-Zone Model of Tissue Damage by a CO2 Laser," Phys. Med. Boil, 1986, pp. 967-983, vol. 31, No. 9.

Partovi, F. et al., "A Model for Thermal Ablation of Biological Tissue Using Laser Radiation," Lasers in Surgery and Medicine, 1987, pp. 141-154, vol. 7.

Fitzpatrick, R.E., "Laser Hair Transplanation. Tissue effects of Laser Parameters," Dermatol. Surg., Dec. 1995, pp. 1042-1046, vol. 21. No. 12.

Grevelink, J.M., "Laser Hair Tranplanation," Dermatolog Clinics, Jul. 1, 1997, pp. 479-486, vol. 15, Issue 3.

Rubach, B.W. et al., "Histological and Clinical Evaluation of Facial Resurfacing Using a Carbon Dioxide Laser with the Computer Pattern Generator," Arch. Otolaryngol. Head Neck Surg., Sep. 1997, pp. 929-934, vol. 123, No. 9.

Unger, W.P. et al., "Laser Hair Tranplantation," J. Dermatol. Surg. Oncol., Aug. 1994, pp. 515-521, vol. 20, No. 8.

Unger, W.P. "Laser Hair Transplanation III. Computer-Assisted Laser Tranplanting," Dermatol. Surg. Dec. 1995, pp. 1047-1055, vol. 21, No. 12.

European Office Action, European Application No. 00916279.3, Aug. 28, 2006, 4 pages.

European Office Action, European Application No. 00916279.3, Dec. 15, 2006, 4 pages.

European Search Report, European Application No. 00916279.3, May 11, 2005, 2 pages.

Nelson, J.S. et al., "Dynamic Epidermal Cooling in Conjunction with Laser-Induced Photothermolysis of Port Wine Stain Blood Vessels," Lasers in Surgery and Medicine, 1996, pp. 224-229, vol. 19.

PCT international Search Report, PCT/US00/064085, Jul. 88, 2000, 1 page.

Fujii, et al., Fibre bundle scanner for laser photocoagulation treatment. Optics and Laser Technology, Feb. 1982, pp. 39-41.

Fujii, et al., Multispot laser photogoagulation system using a fiber bundle scanner, Applied Optics, vol. 21, No. 19, Oct. 1982, pp. 3437-3442.

Apfelberg, et al., Dot or Pointillistic Method for Improvement in Results of Hypertrophic Scarring in the Argon Laser Treatment of Portwine Hemangiomas, Lasers in Surgery and Medicine, 6:552-558 (1987).

Apfelberg, Intralesional Laser Photocoagulation—Steroids as an Adjunct to Surgery for Massive Hemangiomas and Vascular Malformations, Atherton Plastic Surgery and Laser Center, Atherton, CA 1995, pp. 144-149.

Manstein, D. et al., "Spatially Confined Photothermolysis of dermal targets using an IR-fiberlaser in combination with focusing and contact cooling," American Society for Laser Medicine and Surgery, 2002, Abstract 92, p. 28.

* cited by examiner

FIG. 7A1 585 nm
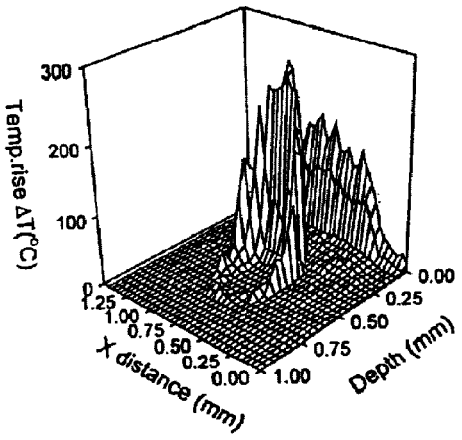
FIG. 7B1 585 nm
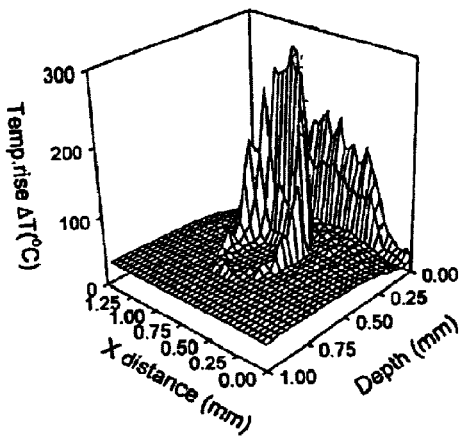
FIG. 7A2 632 nm
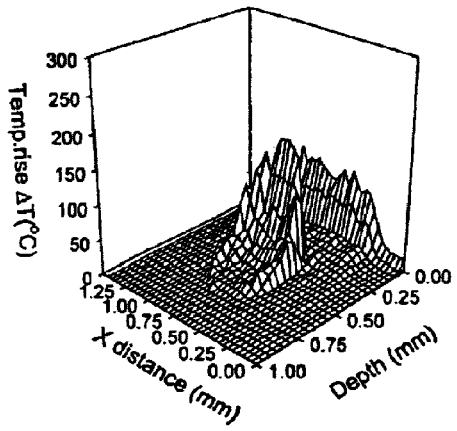
FIG. 7B2 632 nm
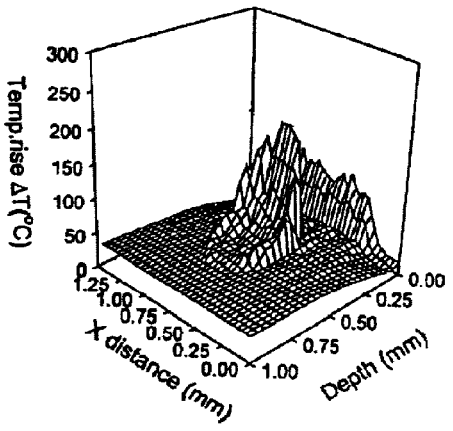

FIG. 7A3
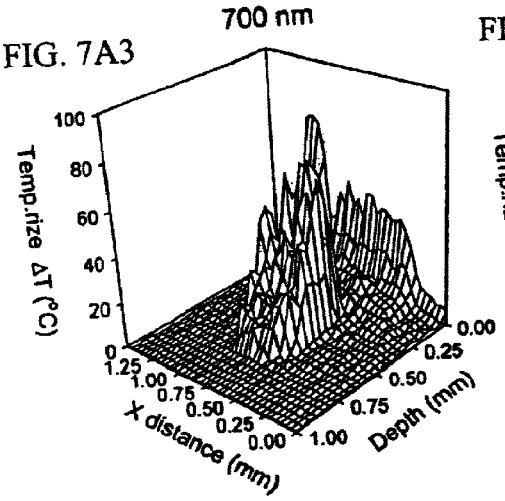
FIG. 7B3
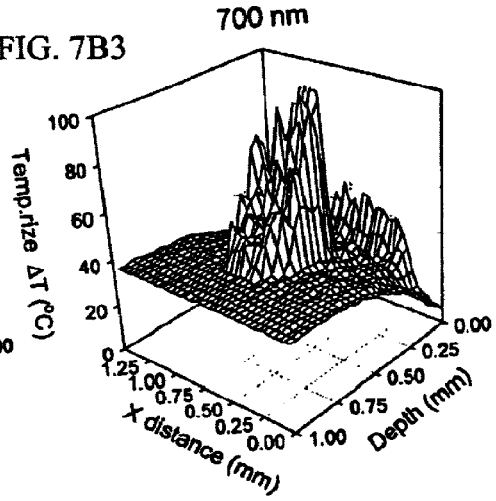
FIG. 7A4
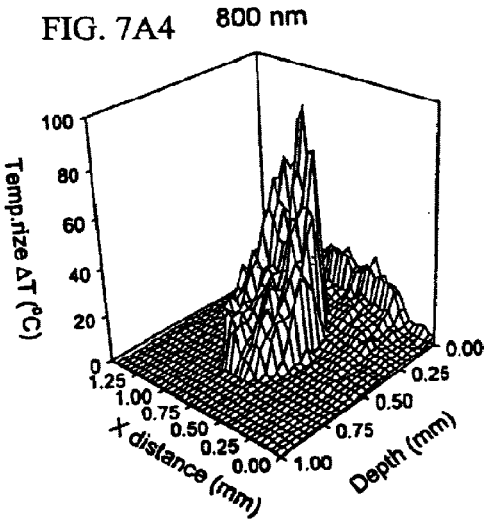
FIG. 7B4
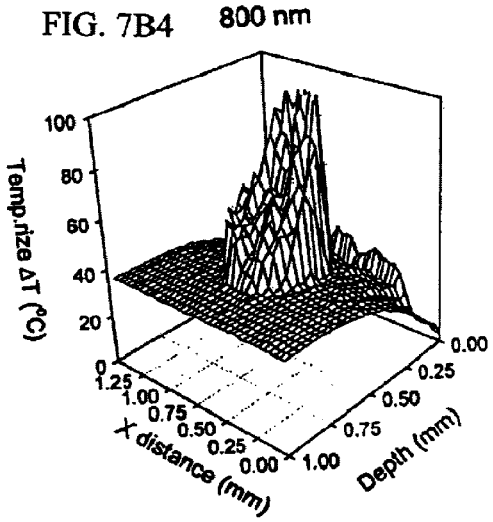

FIG. 7A5 1064 nm
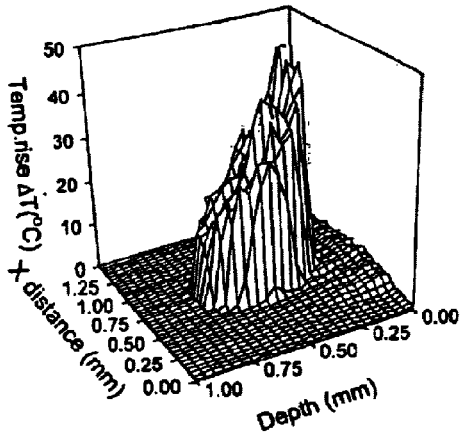
FIG. 7B5 1064 nm
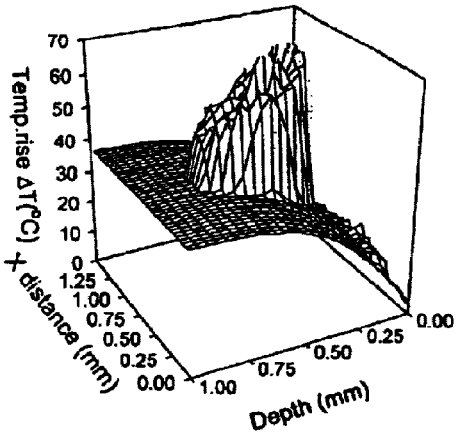
FIG. 7A6 1340 nm
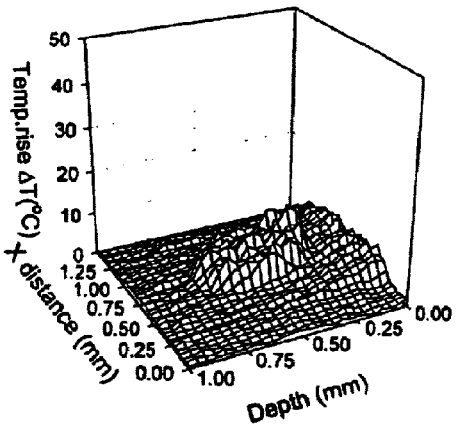
FIG. 7B6 1340 nm
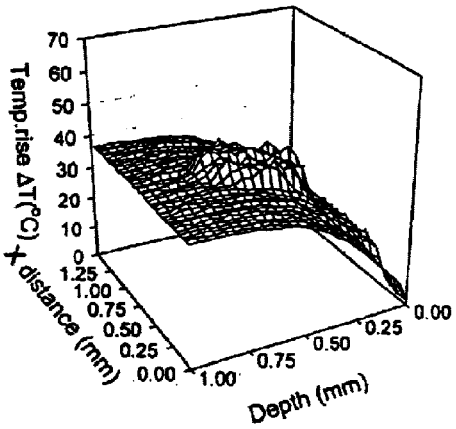

FIG. 7A7
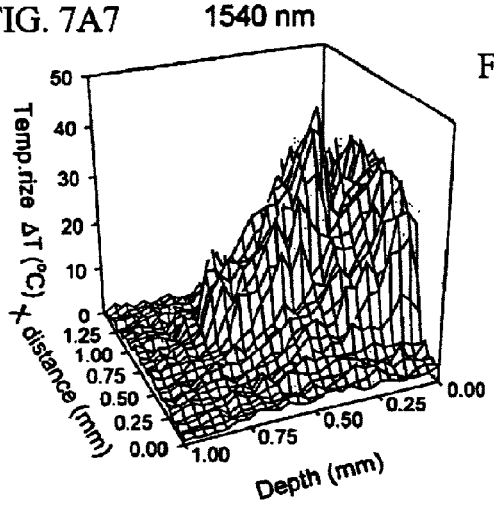
FIG. 7B7
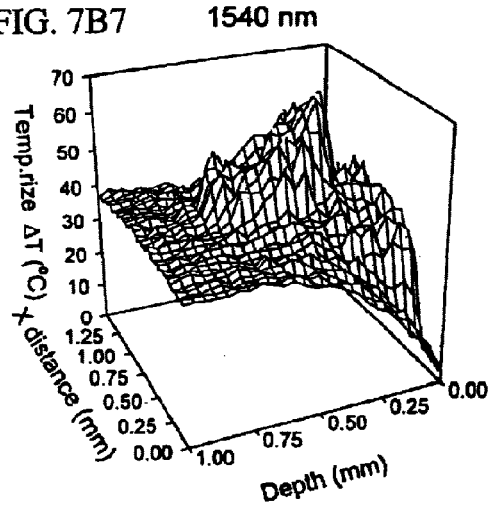

FIG. 8A
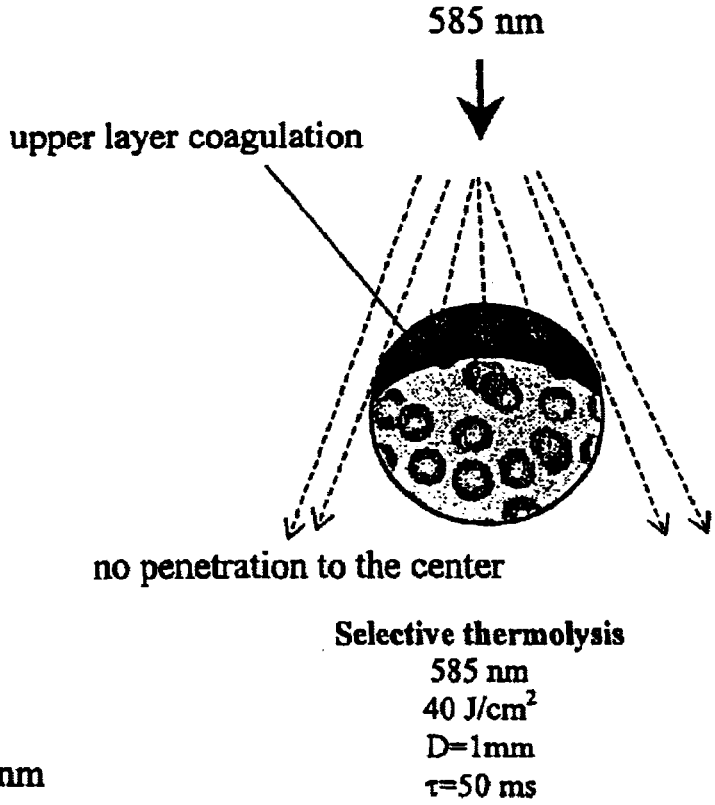
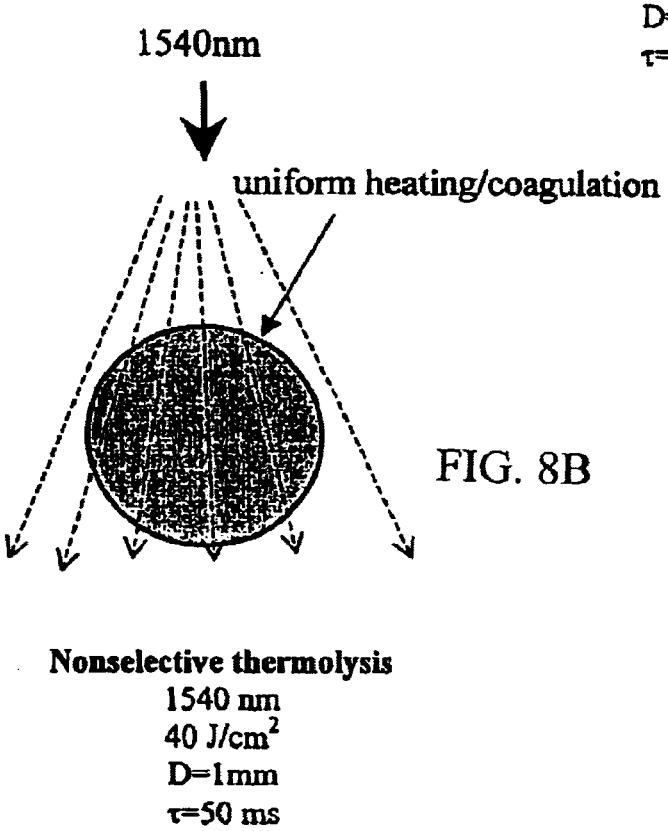
FIG. 8B

FIG. 10A
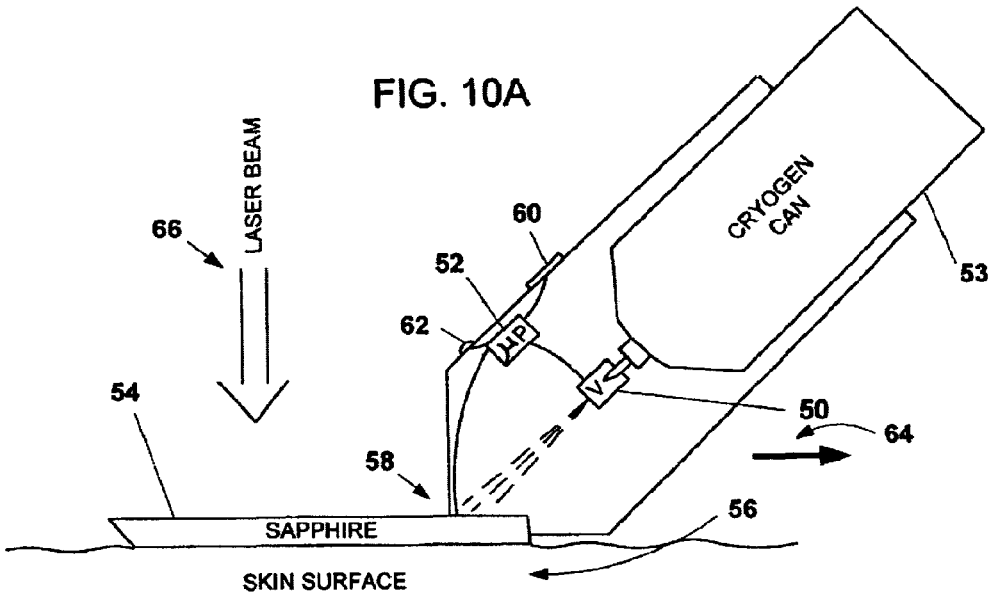
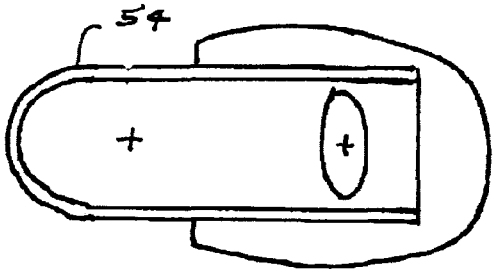
FIG. 10B

METHOD FOR CRYOGENICALLY TREATING TISSUE BELOW THE SKIN SURFACE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS-REFERENCE TO RELATED APPLICATIONS*

[This application is a continuation-in-part application of U.S. Ser. No. 09/174,065 filed Oct. 16, 1998 U.S. Pat. No. 6,059,820. This invention relates to devices and methods for laser treatment and in particular to laser treatment with surface cooling.] *This application is a continuation reissue application of Reissue application Ser. No. 11/250,139, filed Oct. 13, 2005, which is a reissue application of U.S. Pat. No. 6,632,219 (application Ser. No. 09/523,225, filed Mar. 10, 2000), which is a continuation-in-part of application Ser. No. 09/174,065, filed Oct. 16, 1998 and now U.S. Pat. No. 6,059,820. Reissue application Ser. No. 11/250,139 is hereby incorporated by reference herein in its entirely for all purposes. Notice: More than one reissue application has been filed for the reissue of U.S. Pat. No. 6,632,219. The reissue applications are Reissue application Ser. No. 11/250, 139 (now U.S. Pat. No. Re. 42,594), continuation Reissue application Ser. No. 13/165,153 (now U.S. Pat. No. Re. 43,881), and continuation Reissue application Ser. No. 13,165,181 (the present application), all of which are reissues of U.S. Pat. No. 6,632,219.*

BACKGROUND OF THE INVENTION

1. Prior Art Skin Cooling

The principal methods presently used for skin cooling before or during the laser treatment involve the use of a cold contacting window or cryogenic spray device. Cryogenic spray directly to the skin may reduce a skin temperature below 0 C but can freeze the skin and cause significant damage to it. Typical cold contacting windows of the prior art utilize ice water at 0 C can cool the surface of the skin to as low as about 4 C. But prior art ice water cooled cold contact window devices are inadequate to remove enough heat to prevent unwanted surface tissue damage in many applications.

Three prior art techniques are described in the following United States patents: C. Chess, Apparatus for treating cutaneous vascular lesions, U.S. Pat. No. 5,486,172; Anderson et al., U.S. Pat. No. 5,595,568; and C. Chess, Method for treating cutaneous vascular lesions, U.S. Pat. No. 5,282,797. All of these devices and methods provide for the cooling of the skin down to temperatures of about 4 C but not below it.

A different technique is described by J. S. Nelson et al., in the article "Dynamic Epidermal Cooling in Conjunction With Laser-Induced Photothermolysis of Port Wine Stain Blood Vessels, Lasers in Surgery and Medicine 1996;19: 224-229. In this technique the direct cryogenic spray to the skin surface is used before the laser pulse delivery. This method is normally not satisfactory. The surface gets too cold and the subsurface layers are not sufficiently cooled so that unwanted damage occurs at the surface because the tissue gets too cold from the cryogen and/or unwanted damage occurs in the immediate subsurface layers because the tissue gets too hot from the laser beam.

2. Selective Photothermolysis

Dr. Leon Goldman and Dr. Rex Anderson developed the technique known as selective photothermolysis. This technique involves the use of a laser beam having absorption in targeted tissue much higher than in other tissue. Blood has very high absorption of laser radiation at about 530 nm and 575-590 nm. These frequencies are available from the double frequency Nd-YAG laser producing 532 nm light and by an argon laser producing 530 nm. Dye lasers at 577, 585 and 587 are also used in techniques that target blood vessels. These techniques have proven very successful in treating conditions known as port wine stains when the blood vessels are small and near the skin surface. The techniques do not work well for deeper, larger blood vessels.

What is needed is a better laser surgery cooling method to better control tissue temperature during laser treatments.

SUMMARY OF THE INVENTION

The present invention provides a laser treatment device and process with controlled cooling. The device contains a cooling element with high heat conduction properties, which is transparent to the laser beam. A surface of the cooling element is held in contact with the tissue being treated while at least one other surface of the cooling element is cooled by the evaporation of a cryogenic fluid. The cooling is coordinated with the application of the laser beam so as to control the temperatures of all affected layers of tissues. In a preferred embodiment useful for removal of wrinkles and spider veins, the cooling element is a sapphire plate. A cryogenic spray cools the top surface of the plate and the bottom surface of the plate is in contact with the skin. In preferred embodiments the wavelength of the laser beam is chosen so that absorption in targeted tissue is low enough so that substantial absorption occurs throughout the targeted tissue. In a preferred embodiment for treating large spider veins with diameters in the range of 1.5 mm, Applicants use an Er:Glass laser with a wavelength of 1.54 microns. In another embodiment a cooling rod is used. A first surface is in contact with the skin surface being treated and an opposite surface is contained in an anticondensation oil chamber that is optically connected to a laser beam delivering fiber optic cable. In this preferred embodiment the temperature of the rod is monitored with a thermocouple which provides a feedback signal to a processor which controls the cooling and the laser power to provide proper regulation of temperatures at all affected tissue layers. Preferred embodiments the device may be used for treating port wine stains especially those stains involving relatively deep larger blood vessels which as indicated in the Background section are not well treated with photothermalyses techniques using highly preferentially absorbed wavelengths of about 530 nm and 575 to 590 nm.

BRIEF DESCRIPTION OF THE DRAWINGS

FIGS. 7A1-7 and 7B1-7 are temperature profile charts.

FIGS. 8A and 8B show the effect of two different wavelength beams on a blood vessel.

FIGS. 10A and 10B show a preferred embodiment of the present invention.

DETAILED DESCRIPTION OF PREFERRED EMBODIMENTS

Preferred embodiments of the present invention can be described by reference to the figures.

COOLING AND SUBSURFACE LIGHT DELIVERY METHOD

Skin Surface Cooling

Figure 1:
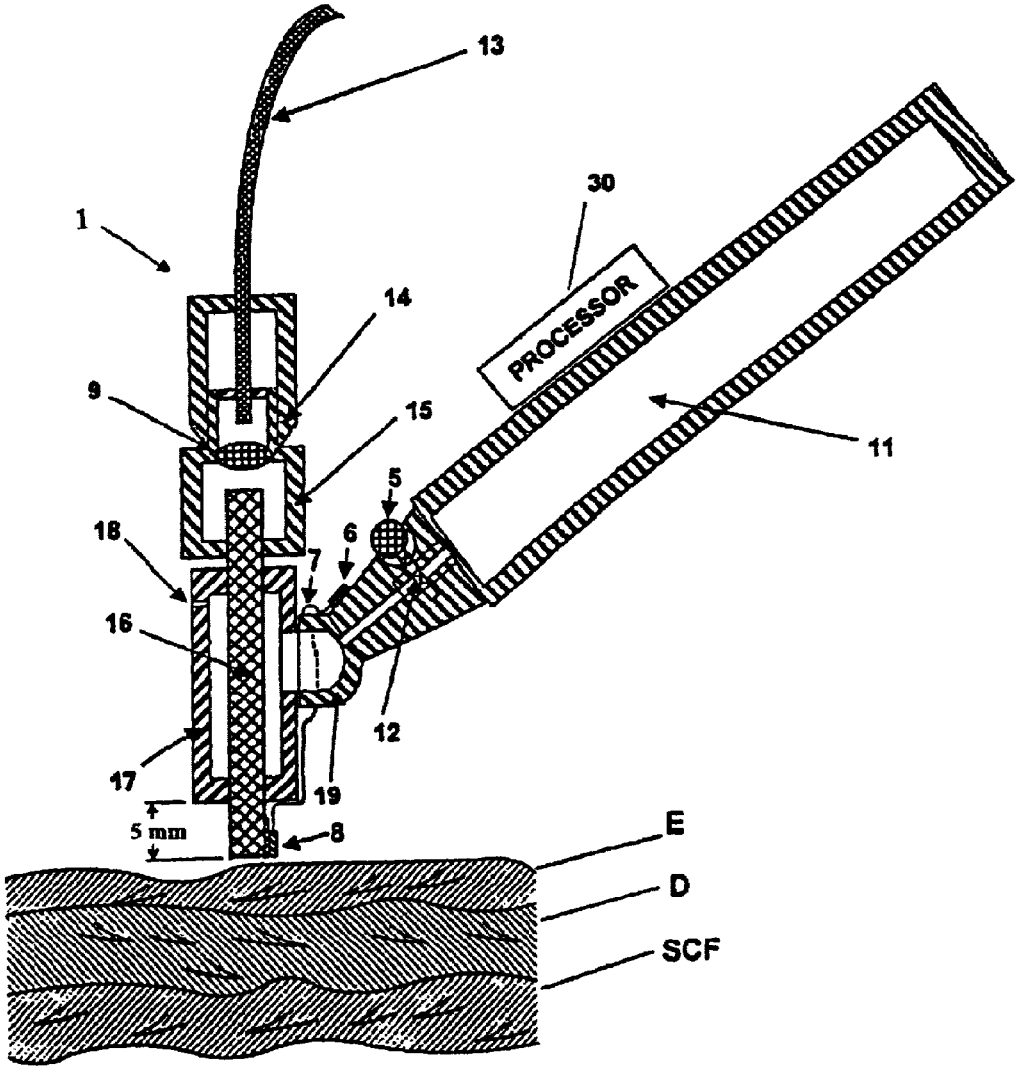
FIG. 1 is a drawing of the cooling rod hand piece for the subsurface light energy delivery with circumferential cooling of the cooling rod.

A section of human skin with a cooling cryogenic rod device 1 in accordance with the present invention is shown in FIG. 1. FIG. 1 shows a cryogenic container 11 that also serves as a handle for the device. A nozzle 19 with a valve 12 and a valve-opening actuator 5 provides for a cryogenic spray onto the portion of sapphire rod 16 within cryogenic cooling chamber 17. In this embodiment the cryogen is Tetrafluoethan. The cryogenic mist exhausts through port 18. An anti condensation oil chamber 15 contains collimating lens 9, a fiber holder 14 optically connecting delivery fiber optic cable 13 and a transparent optical oil, which in this embodiment is microscopic immersion oil. In this embodiment the laser beam is provided by an Er:Glass pulse laser producing 25 Joule 2 ms pulses at a wavelength of 1.54 microns and at pulse rates of 1 Hz or 0.5 Hz. The spot size is about 7 mm2. The laser output is adjusted to provide energy fluence on the skin surface of about 25J/cm2 per pulse. With a spot size of 7 mm2, the energy per pulse is about 1.7J. A thermocouple 8 is insulated from rod 16 and senses the temperature of the skin surface and provides a feedback signal to processor 30 which controls delivery of the cryogen spray via actuator 5 and the laser pulses through the laser controls (not shown). Also shown on FIG. 1 is "ready" light 7 and battery 6 which powers the light and the thermocouple. FIG. 1 also shows a section of human skin including epidermis E, dermis D and a subcutaneous fat SCF.

The section of skin is first cleaned with alcohol to remove moisture to prevent a condensation on the contacting surface of the rod and in order to dehydrate the skin surface to reduce the epidermal damage from the light interaction with water. When the valve of the nozzle is opened the cryogen coolant is sprayed micro drops into the cooling chamber. The cryogenic mist flows around the sapphire. The micro drops contact the rod and vaporize from the surface of the rod by the rod heat reducing the rod temperature dramatically fast. The whole rod becomes cold almost instantly because of the high thermoconductivity of sapphire. The sapphire rod cools the surface of the skin by heat exchange.

Treatment for Spider Veins with Er:Glass Laser and Surface Cooling

Figure 1A:
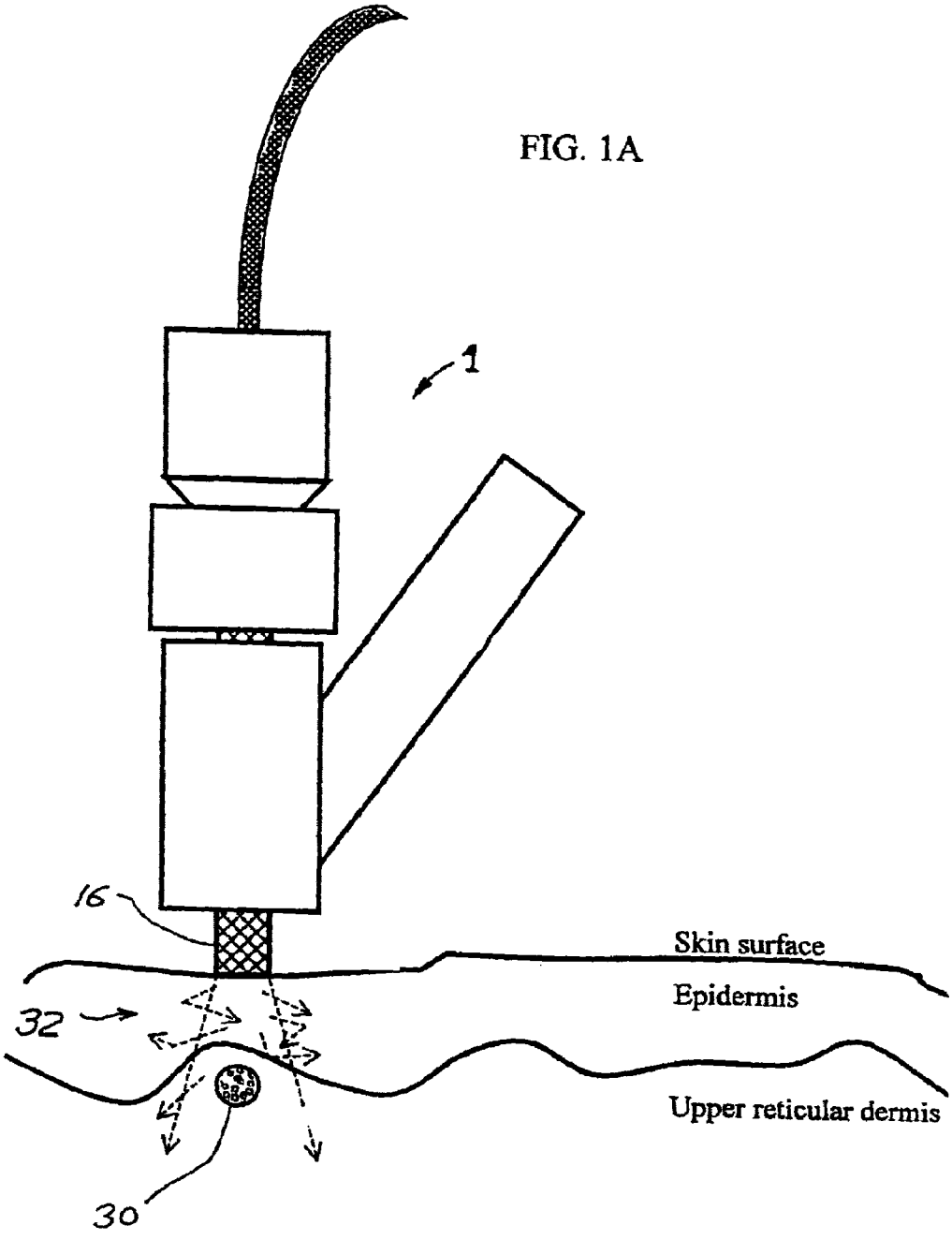
FIG. 1A shows the device being used to coagulate a large blood vessel.
Figure 2:
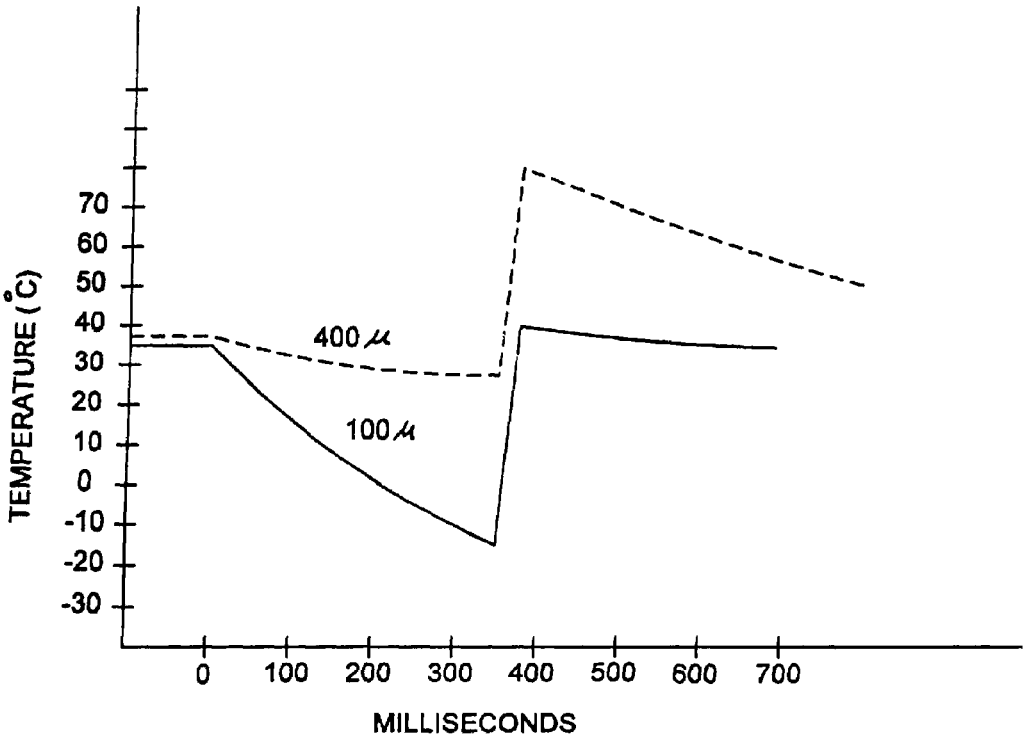
FIGS. 2 is a time graph showing temperature changes below the skin surface.

A preferred application of the device shown in FIG. 1 is for spider vein removal. The operator presses the tip of the device against the skin as shown in FIG. 1 and presses the on button. The processor opens valve 12 permitting cryogen flow. The processor 30 monitors the skin temperature via thermocouple 8 and assures that the skin temperature is not below 0 C for more than 1 second. When processor 30 determines that the temperature of the surface has dropped to a desired low temperature at a desired rate, such as −15 C in a time period of 0.30 to 0.40 seconds, the "lasing" light indicator is switched-on and the processor will direct the laser to fire a pulse. The energy of the 1.7J pulse is dissipated in a distance of about 1.0 mm. With the spot size of about 7 mm2 means that the energy is absorbed in about 0.007 gram of tissue. Since the specific heat of tissue is roughly 4J/gmC, each pulse will heat the skin by an average of about 50 C. But since the energy absorption by blood is about twice that of skin tissue in general, blood temperature is preferably increased about twice as much as the surrounding tissue. Thus, tissue cooled to −15 C will after the laser pulse be at a temperature of about 35 C which is close to normal skin temperature. As shown is FIG. 1A blood in spider vein 30 just below the epidermis which prior to the laser pulse is at a temperature of about 25 C will be heated to slightly over 70 C to destroy the vein tissue. FIG. 2 shows graphs of the temperature of the skin at points 100 microns below the skin surface (near the bottom boundary of the epidermis) and 400 microns below the surface of the skin (at the center of a 200 micron diameter spider vein) during the above described process. The reader should note that the tissue at a depth of 100 microns is below 0 C for about 100 milliseconds and that the tissue at 400 microns is above 70 C for about 100 milliseconds. It is well known that tissue is not adversely affected by subfreezing temperatures in this range until the time periods are more than about 500 ms. On the other hand, however temperatures in excess of 70 degrees for about 10 ms will coagulate the tissue.

Figure 8C:
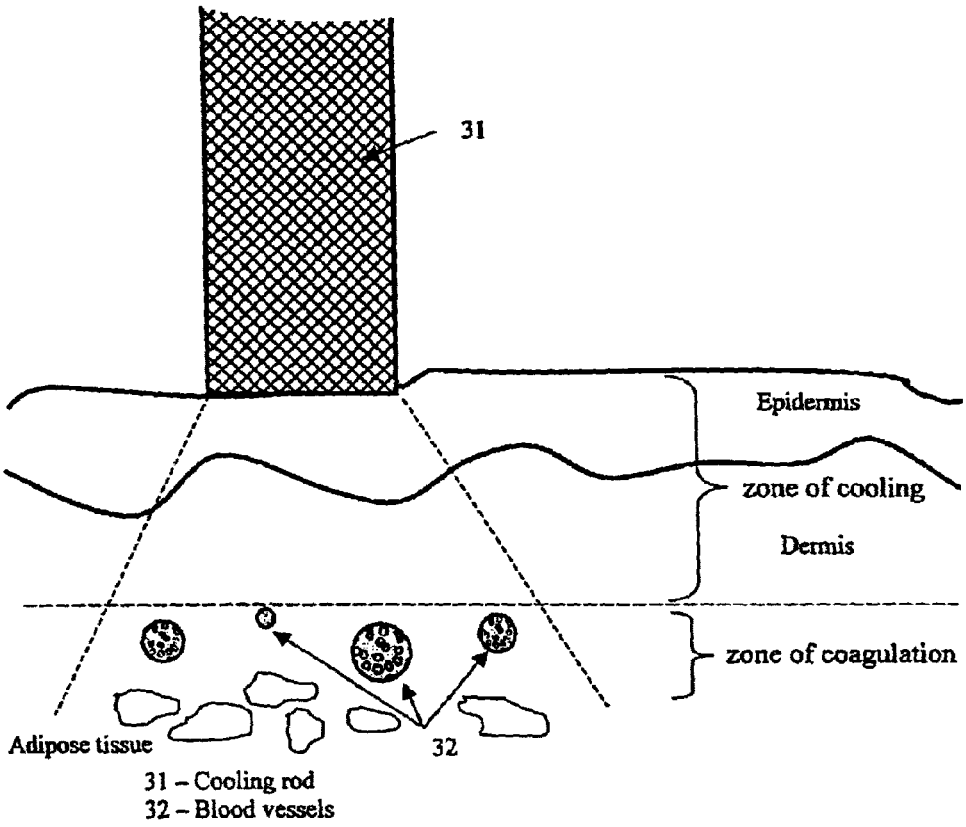
FIG. 8C shows blood vessel coagulation.

The processor will stop the lasing if thermocouple 8 indicates an excessive temperature which in this procedure would be about 60 C. The thermocouple 8 is preferably calibrated to the temperature of the skin located in one millimeter from the rod edge. The difference between the temperature of the skin under the rod and in 1 mm from the rod edge is varied from 10 C to 20 C and depending upon the rod design. Applicant has performed computer simulations to determine temperature profiles in the case of laser treatments, at wavelengths of 585 nm, 632 nm, 1064 nm, 1340 nm, and 1540 nm, with and without surface cooling. FIGS. 7A1-7 show the effects of a 20J/cm$^2$, 0.54 mm diameter blood vessel, and 0.5 mm below the skin surface, with no surface cooling. FIGS. 7B1-7 represent similar conditions with surface cooling with a −15° C. sapphire glass rod for 0.5 sec. These simulations show the advantages of the Nd:YAG at 1064 nm, the Nd:YAP at 1340 nm and the Er:Glass at 1540 nm as compared to the shorter wavelength lasers that are more highly absorptive in blood. This effect is seen clearly by comparing FIG. 8A to FIG. 8B. As shown in FIG. 8A the 585 nm pulse coagulates blood at the top of the vessel but does not penetrate sufficiently to coagulate blood deeper in the vessel. On the other hand the 1540 nm pulse provides substantially uniform heating and coagulation of the vessel. FIG. 8C shows zones of cooling and coagulation in skin tissue.

Mechanical contact, optical, electrical or other sensor can be used to trigger the time delay circuit after the cold rod touches the skin for the definite time. The time delay is defined by the procedure and by the anatomical structure of the skin and blood vessel.

Treatment for Wrinkles with Er:Glass Laser

It is known that an effective treatment for the removal of wrinkles is to destroy a line of tissue just below the epidermis at the bottom of the wrinkle valley. Scar tissue forms in the place of the destroyed tissue pushing up the bottom of the valley and effectively removing the wrinkle. The problem is how do you destroy the tissue below the epidermis without also destroying the epidermis and thus replacing an ugly wrinkle with an ugly scar. The present invention provides the solution. Using substantially the same procedure as described above, the tissue at the bottom of the wrinkle valley is destroyed without any significant damage to the epidermis. Details and parameters are outlined below.

Er:Glass Laser

The laser device used in this preferred embodiment is a free running mode Er:Glass pulse laser that has the spike in the range of 1.54 microns. Light in this range has minimal scattering losses in the skin tissue and is readily absorbed in the skin fluids. Laser parameters such as pulse width, energy density, repetition rate can be selected to best fit the skin and the treated lesion of the patients. The parameters for two specific examples which have been utilized with good results for wrinkle removal and leg vein treatment are shown in Table 1:

TABLE 1

Parameters Preferred.

| | Wrinkles | Spider Veins |
|---|---|---|
| Pulse Width | 2 ms | 2 ms |
| Repetition Rate | 1 Hz | 0.5 Hz |
| Sapphire Rod Diameter | 3 mm | 2 mm |
| Spot Size | 7.2 $mm^2$ | 3.14 $mm^2$ |
| Energy Fluence | 25 $J/cm^2$ | 25 $J/cm^2$ |

Each point on the skin receives a high energy density illumination for about 2 milliseconds. Some of the light is reflected. Of the light which is not reflected a significant portion of the energy of each pulse penetrates to the depth up to 1-1.5 mm and is absorbed by the skin fluids.

Operating within the parameters specified is important. They have been chosen to preferentially cool the skin surface protecting epidermis and to heat the subepidertnal collagen or blood vessels to the level of irreversible changes in the coagulated skin tissue and blood vessel proteins. It must be chosen so that a large amount of energy is deposited in the skin quickly so that the temperature of the targeted tissue rises rapidly to about or slightly above 70° C. The cooling applied to the surface for about half a second is enough to protect epidermis from the temperature increasing to 70 C. Thus the above procedure can be used effectively for treatment spider veins.

Nd:YAG Laser

In another embodiment of the present invention the Nd:YAG laser is used. The wavelength of the beam is at 1.06 microns. Light at this wavelength has a very low absorption in skin tissue and in interstitial fluids. Absorption in blood is also low but is about twice that of general skin tissue and interstitial fluids. Therefore, this wavelength is very good for treating telagiactasia with dimensions in the range of 1 mm and greater and large spider veins in the range of 1.5 mm. Table 2 gives some preferred parameters for treating a 1 mm telagiactasia and a 1.5 mm-spjider vein.

TABLE 2

Parameters Preferred.

| | Telagiactasia 1 mm | Spider Veins 1.5 mm |
|---|---|---|
| Pulse Width | 25 ms | 50 ms |
| Repetition Rate | 1 Hz | 2 Hz |
| Sapphire Rod Diameter | 3 mm | 10 mm |
| Spot Size | 7.2 $mm^2$ | 78.5 $mm^2$ |
| Energy Fluence | 40 $J/cm^2$ | 60 $J/cm^2$ |

Long Pulse Nd:YAG for Deep Treatment

A long pulse Nd:YAG with a pulse width of about 100-200ms. Pulses in this range have been utilized with good results for destruction of skin tumor angiogenesis and coagulation of hair follicular blood vessels at depths of up to 5.0 mm. Some preferred parameters are given in Table 3. Preferably, cooling is provided for a period of about 1 to 2 seconds prior to the illumination.

TABLE 3

Parameters Preferred.

| | Angiogenic Plesus 0.8 mm | Follicular Plexus 1 mm |
|---|---|---|
| Pulse Width | 100 ms | 150 ms |
| Repetition Rate | 1 Hz | 1 Hz |
| Sapphire Rod Diameter | 10 mm | 12 mm |
| Spot Size | 78.5 $mm^2$ | 113 $mm^2$ |
| Energy Fluence | 120 $J/cm^2$ | 140 $J/cm^2$ |

Computer Simulations of Temperature Rise in Human Skin

Estimation of temperature rise in skin can be made by calculating laser light fluence in skin and estimating energy deposition per unit volume of skin. Effect of contact skin surface cooling was accounted based on the solution of heat transfer equations.

In order to choose proper light fluence in skin the following optical properties of tissue have been used:

| | Absorption coef (1/cm) | Scattering coef (1/cm) | Asymmetry Factor (g) | Refr. Index n | Thickness |
|---|---|---|---|---|---|
| Epidermis | 5 | 300 | 0.8 | 1.4 | 100 micron |
| Dermis | 5 | 100 | 0.85 | 1.4 | Semiinfinite |
| Blood | 10 | 300 | 0.98 | 1.4 | N/A |

At a wavelength of 1.54 micron, absorption in tissues is determined primarily by their water content. Water content of whole blood is more then 90%, whereas in dermis and epidermis it is about twice less. For this reason absorption of IR radiation and temperature rise in blood is about two times higher than in surrounding dermis tissue. Once fluence in the skin is calculated and a depth of absorption is estimated, the temperature rise $\Delta T$ due to light absorption can be roughly estimated as follows:

$$\Delta T = Q/mc$$

where skin density is about 1.15 g/cm$^3$ and specific heat of skin about 3.8J/Cgm.

Effect of skin surface cooling on temperature distribution in skin have been estimated by solving heat transfer equation in semi infinite skin tissue with boundary conditions corresponding to constant −5° C. temperature of the surface (or other constant temperature of the sapphire rod). Temperature distribution in ° C. in skin then can be calculated by formula:

$$T(z,t)=37*\mathrm{erf}(z/2\ \alpha ct),$$

where erf refers to the Gausian error function, and z is the depth into the tissue, t is time lapse in seconds from the start of the contact skin cooling and $\alpha=10^{-4}(\mathrm{cm}^2/\mathrm{sec})$ is thermal diffusivity of skin dermis. Skin temperature was found by superposition of laser heating and surface cooling effects.

Various elaborate computer programs are available for more precise estimate of temperature distribution within the skin as a function of time. Applicants have made analysis using a Monte-Carlo computer code specifically modified for skin thermodynamic analysis and some of the results are shown in FIGS. 7A1-7 and 7B1-7 which were discussed above. Cooling experiments have been performed by using different configurations of the cooling element for the different applications. For these applications, one of the alternative embodiments is recommended.

Testing of the Devices

The reader should understand that devices according to the present invention work by destroying living tissue. Hopefully the destroyed tissue is unwanted tissue and is quickly replaced by new tissue produced by the body's natural ability to repair damaged and destroyed skin tissue. Care should be taken to minimize unwanted tissue destruction. Applicants recommend that tests be performed prior to use of the device in the manner disclosed above. A test station could be constructed using a plastic material having thermal properties similar to human skin and equipping it with fast response thermocouples located at various depths and positions below the surface. The thermocouples should be connected to the real time monitors so that the technician and the patient can see the thermal effects produced by the device prior to actual use on the patient.

CRYOGENICALLY COOLED SELF CONTAINED WINDOW

Figure 5A:
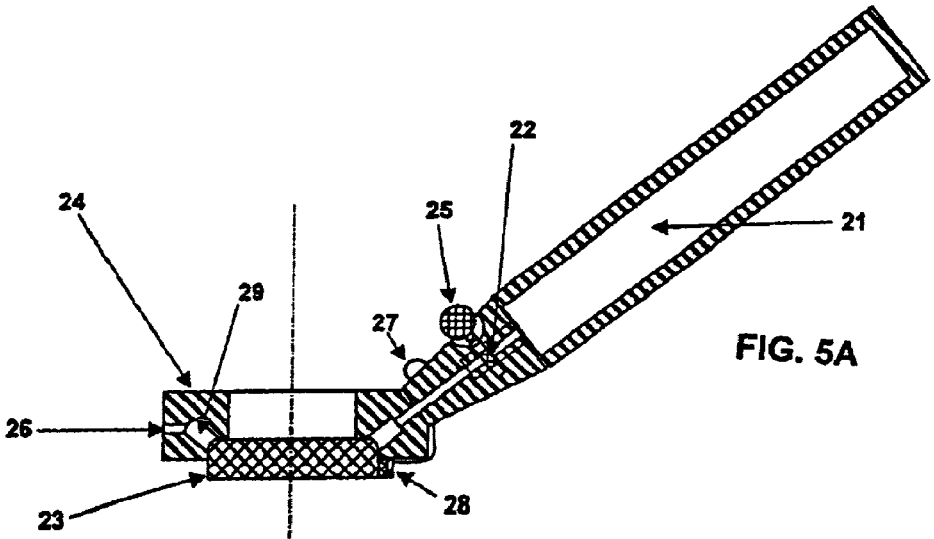
FIGS. 5A and 5B is a second preferred embodiment.
Figure 5B:
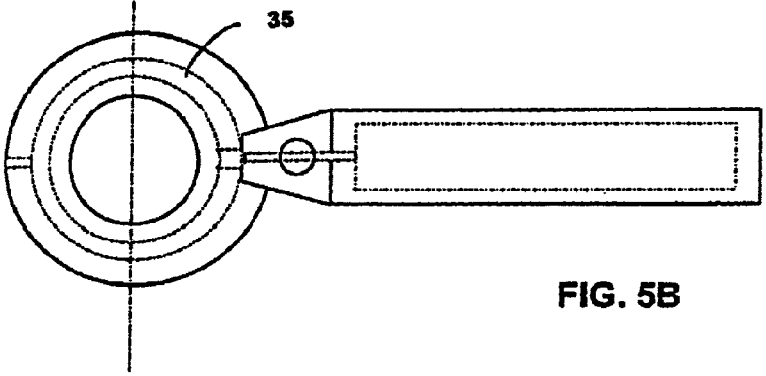

A second embodiment involves the use of a cryogenically cooled diamond cooling element as shown in FIGS. 5A and 5B. The device consists of copper holder 24, which has a cryogenic container 21. Synthetic diamond cooling element 23 is in the shape of a flattened cylinder and contains a circular groove through which cryogenic mist flows. The mist exits at the exit port 26.

The flattened diamond rod is transparent to the laser beam. It is applied to the part of the cleaned skin to be treated. The nozzle valve opens the shutter and the cryogenic spray flows to the chamber around this window. When the window is cold the "ready" light will be switched-on. The energy delivery procedure can be started. This device is good for the large area irradiation such as subsurface tumor interstitial thermotherapy with a high frequency electromagnetic radiation.

PATERNED COOLING ELEMENT FOR MASKING PORTIONS OF TISSUE

Figure 3A:
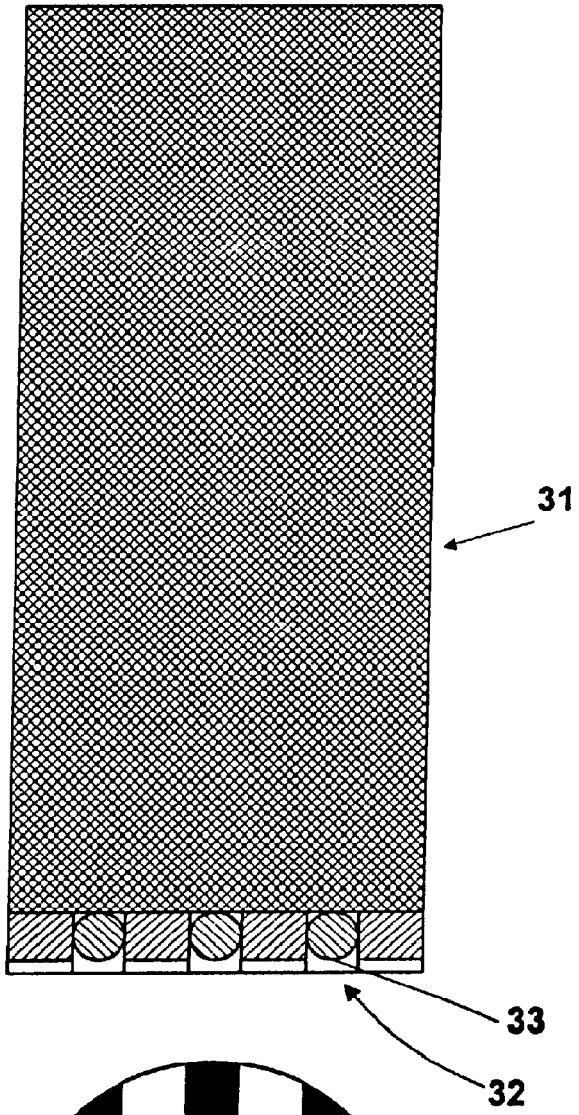
FIGS. 3A and 3B show a partially masked cooling rod.
Figure 3B:
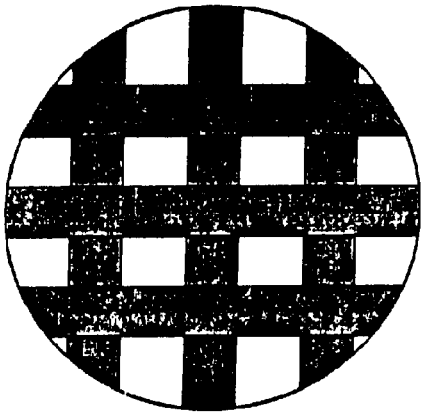

A third embodiment for practicing this invention is to use a patterned rod to the surface of the skin in order to have damaged and healthy areas under the skin surface. FIGS. 3A and 3B show rod 31 with the perpendicular grooves 32 filled with copper stripes 33.

A laser light is sent through the cooled rod to the surface of the skin does not penetrate through the copper stripes. But the contacting surface of the rod has an almost uniform temperature distribution. It means that the surface of the skin is cooled uniformly. But under skin damage is not uniform having irradiated and not irradiated healthy spots. The reason to have these healthy untouched spots around the damaged tissue is to use the capacity of healthy spot tissue and cells for the fast immune response and wound healing process.

SELF COLLIMATED COOLING ELEMENT

Figure 4:
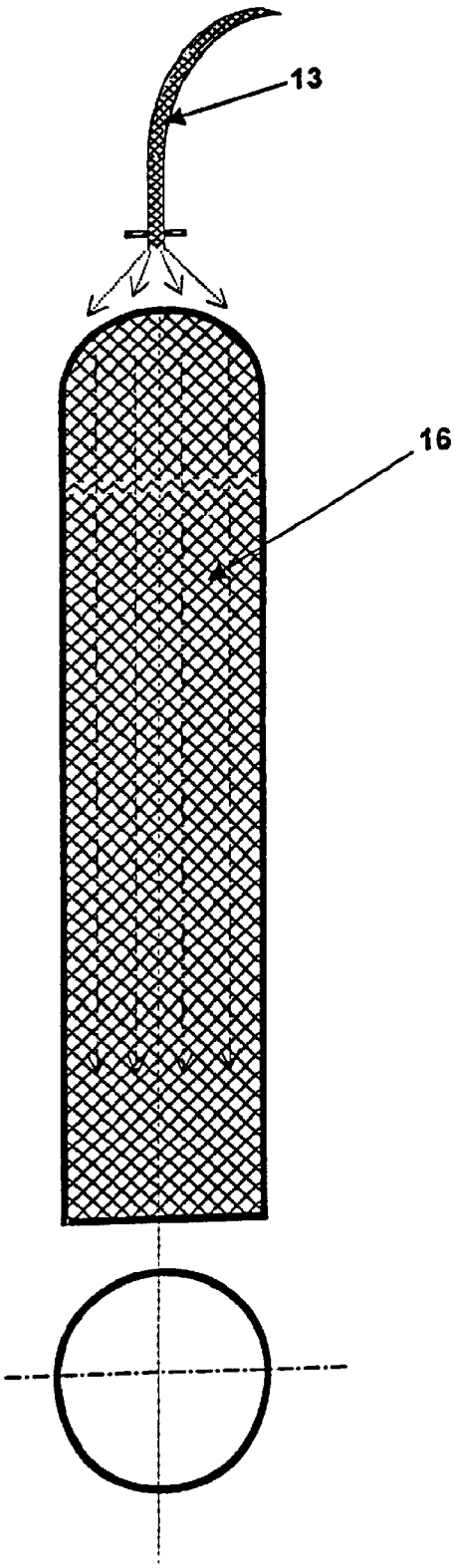
FIG. 4 shows a rod with the lens-type tip surface.

This embodiment is essentially the same as the first one described above except that the rod tip, which is connected to the fiber optics has concave form for the self-collimating beam properties. FIG. 4 shows a cooling element with the lens-type tip surface. For such an element, it does not require a collimated lens and can be replaced by the transparent disk-type window in the oil chamber.

HORIZONTAL AND ANACHROMATIC COOLING ELEMENT

Figure 6A:
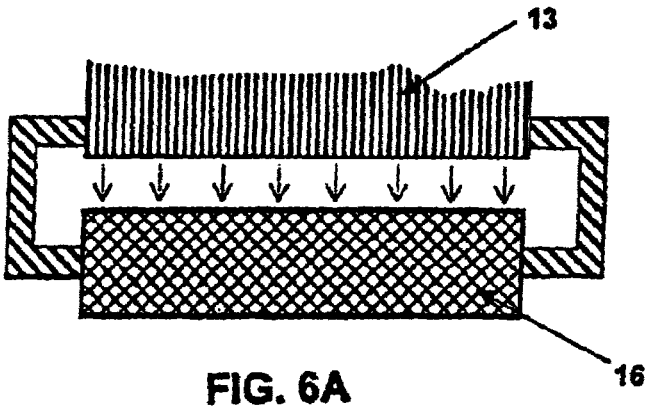
FIG. 6A and 6B show a drawing of the horizontally positioned cooling rod.
Figure 6B:
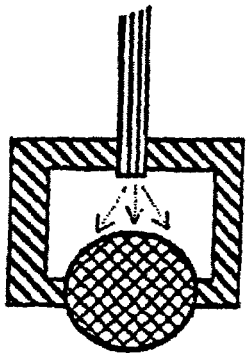

This embodiment is essentially the same as the first one described above except that the cylindrical element is placed in the cooling chamber horizontally (see FIGS. 6A and 6B). The reader should note that the rod could be of different shapes to provide desired beam profiles on the skin surface or to focus the beam. The focal point (or focal line) could be under the skin to help concentrate the beam energy in target locations.

TISSUE DESTRUCTION WITH FREEZING

The device disclosed herein can be used in reverse. That is, surface tissue destruction can be provided by the very cold surface of the tip of the sapphire rod. Preferably, the skin is pre-warmed with a low energy laser pulse of about one-half the values specified above which should cause no damage but will provide warmth which will minimize tissue destruction caused below the surface. This process is good for freezing of warts and certain types of surface skin cancers.

PRE AND POST COOLING

Figure 9:
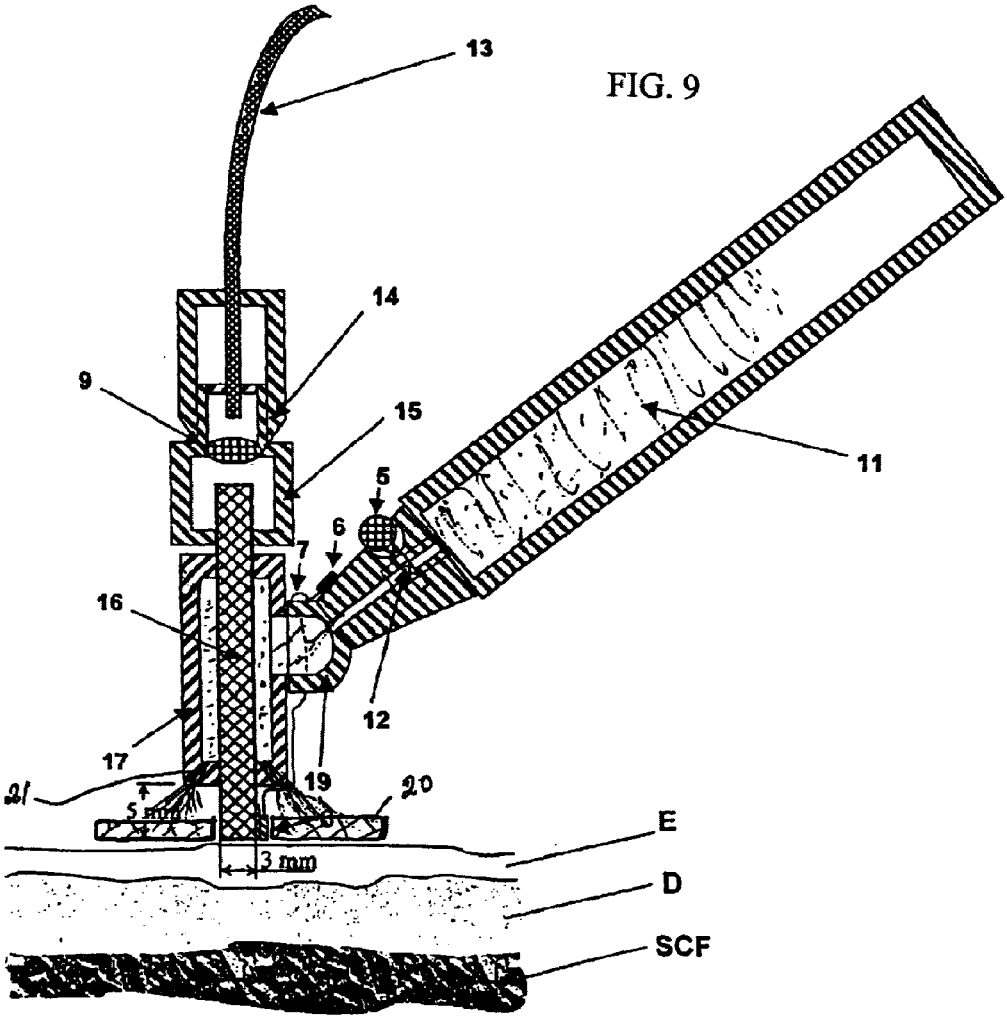
FIG. 9 is a drawing of a preferred embodiment using a plate-type cooling element with non-circumferential cooling of the cooling element.

In an additional embodiment pre and post cooling is provided by transparent circular part 20 as shown in FIG. 9 preferably comprised of sapphire. In this case the exhaust from chamber 17 flows through port 21 onto the surface of the circular sapphire part 20 to cool it. This cool surface which will be at a temperature above 0 C prevents the epidermis from being overheated from the hotter lower dermis. This permits the technician to move the laser beam rapidly across the skin surface. The illuminated portion of the skin is both pre-cooled and post-cooled.

PLATE TYPE COOLING ELEMENT

Another preferred embodiment is shown in FIGS. 10A and B. Solenoid valve 50 is controlled by microprocessor 52 to provide a controlled spray from cryogen can 53 on sapphire plate 54 which cools skin surface 565. The temperature of plate 54 is monitored using thermocouple 58. Temperature data is displayed on display 60. The operator has manual control of the spray with switch 62 as desired or the spray can be automatically controlled with processor 52 based on temperature data from thermocouple 58. In a preferred process the operator holds a laser device in one hand and the cooling device in the other. He moves the cooling device in the direction of arrow 64 and the laser beam is directed as shown at 66. As in the paragraph above sapphire plate 54 provides both pre and post cooling as the cooling device is moved along the skin surface. FIG. 10B shows a bottom view of plate 54. In this example the laser beam applicator (not shown specifically) and the cooling device are handled separately, but they could be mounted together as one unit.

OTHER EMBODIMENTS

It is very important for all of these embodiments and in other embodiments that will be apparent to persons skilled in the art that the cooling rod has a very high thermoconductivity coefficient and low absorption of the irradiating light. The substance used for the cryogenic cooling can be chosen based on the particular application. The important thing is to use a proper time of cooling in order to reach a required low temperature of the tissue at the required depth. Persons skilled in the art will recognize that certain material and configuration of the rod, container, coolant and connector will be preferred for different skin type, different lesions and different applications. The reader should note that the preferred embodiment of this invention can be used without this laser to provide cryogenic treatment to surface skin lesions. The same skin cooling can be provided with about 1/10 the cryogen as direct open spray. An important application of the device for cryogenic treatment is to promote lymphatic drainage by cold therapy. Skin rejuvenation begins with flushing of the lymphatic system to remove dead proteins and other debris. Thermal receptors in the lymphatic system are effectively stimulated by the presence of cold applied to the skin surface. Current techniques for lymphatic drainage by cold therapy include spray and ice, both of which are messy and offer poor control of the skin temperature. The device shown in FIGS. 10A and B is useful for lymphatic drainage due to its compact hand held design, disposable canisters and accurate control of the skin temperature.

While the above description contains many specifications, the reader should not construe these as limitations on the scope of the invention, buy merely as exemplifications of preferred embodiments thereof. Those skilled in the art will envision many other possible variations are within its scope. Accordingly the reader is requested to determine the scope of the invention by the appended claims and their legal equivalents, and not by the examples which have been given.

We claim:

[1. A laser system for tissue treatment, comprising:

A) A hand-held portable battery powered tissue cooling unit comprising:

1) a cooling transmitting element comprised of material transparaent to light at a nominal wavelength and having high thermal conductivity and having a contact surface for contacting a surface of tissue being treated, 2) a cryogenic container mounted within or on said cooling unit, 3) a cryogen contained in said container, 4) a cryogenic cooling chamber for cooling at least one surface of said cooling element, said chamber having an entrance port communicating with said container and an exit port, 5) a battery powered cryogenic control means for permitting a flow of vaporizing cryogen from said container into said chamber to cool said at least one surface in order to remove heat from said tissue surface and to produce desired temperature distribution in target tissue being treated, and 6) a battery mounted on or within said cooling unit for providing power to said control means, and B) a source of laser light defining a nominal wavelength arranged to transmit said laser light through said cooling transmitting element.]

[2. A laser system as in claim 1 and further comprising a temperature-monitoring element mounted adjacent to but insulated from said contact surface for monitoring tissue surface temperature.]

[3. A laser system as in claim 1 and further comprising a temperature-monitoring element configured to monitor temperature of said cooling element.]

[4. A laser system as in claim 1 and further comprising a processor programmed for controlling said source of laser light and said flow of cryogen.]

[5. A laser system as in claim 1 wherein said source of laser light is a free running mode Er:Glass pulse laser.]

[6. A laser system as in claim 1 wherein said source of laser light is a Nd:YAG laser.]

[7. A laser system as in claim 6 wherein said Nd:YAG laser is arranged to operate at a pulse width of about 50 ms.]

[8. A laser system as in claim 6 wherein said Nd:YAG laser is arranged to operate at a pulse width of about 100 to 200 ms.]

[9. A laser system as in claim 1 wherein said cooling transmitting element is sapphire plate and substantially all cooling of said plate is through a single non-circumferential surface.]

[10. A laser system as in claim 1 wherein said cooling transmitting element is sapphire rod defining a circumferential surface and substantially all cooling is through said circumferential surface.]

[11. A laser system as in claim 1 wherein said cooling transmitting element is a diamond plate.]

[12. A laser system as in claim 1 wherein said cooling transmitting element is a diamond rod.]

[13. A laser system as in claim 1 wherein said cooling transmitting element is a patterned rod.]

[14. A laser system as in claim 1 wherein said cooling transmitting element has a concave form for self-collimating beam properties.]

[15. A laser system as in claim 1 wherein said cooling transmitting element is a cylindrical rod mounted horizontally.]

[16. A process for treating tissue, comprising the steps of:

A) generating from a source a laser light defining a nominal wavelength,

B) transmitting said laser light through a hand-held portable battery operated tissue cooling unit comprising a cooling transmitting element comprised of material transparent to light at said nominal wavelength and having high thermal conductivity and having a contact surface for contacting a surface of tissue being treated, C) inserting cryogen from a cryogenic container, mounted on or within said cooling unit, into a cryogenic cooling chamber for said cooling element, said chamber having an entrance port communicating with said container and an exit port, wherein said inserting permits a flow of vaporizing cryogen from said container into said chamber to cool said cooling element in order to remove heat from the tissue surface and to produce desired temperature distribution in target tissue and wherein the battery is mounted on or within the cooling unit.]

[17. A process as in claim 16, further comprising the additional step of sliding said cooling element across surface of tissue while applying laser radiation through a portion of said cooling transmitting element so as to provide pre, during and post cooling of said tissue.]

[18. A process as in claim 17, further comprising the step of controlling said source of laser light and said flow of cryogen with a processor programmed with a control algorithm.]

[19. A process as in claim 17, wherein said method is for the purpose of treating spider veins.]

[20. A hand-held portable battery powered tissue cooling unit, useful for both cryogenic tissue treatment and for cooling tissue during laser treatment, comprising:

A) a cooling transmitting element comprised of material transparent to light at a nominal wavelength and having high thermal conductivity and having a contact surface for contacting a surface of tissue being treated, B) a cryogenic container mounted on or within said cooling unit, C) a cryogen contained in said container, D) a cryogenic cooling chamber for cooling at least one surface of said cooling element, said chamber having an entrance port communicating with said container and an exit port, E) a battery powered cryogenic control means for permitting a flow of vaporizing cryogen from said container into said chamber to cool said at least one surface in order to remove heat from said tissue surface and to produce desired temperature distribution in target tissue being treated, and F) a battery mounted on or within said cooling unit providing power to said control means.]

[21. A cooling unit as in claim 20 wherein said cooling transmitting element is comprised of sapphire.]

[22. A cooling unit as in claim 20 wherein said cooling transmitting element is comprised of diamond.]

[23. A cooling unit as in claim 20 wherein said control means includes a temperature detector.]

[24. A cooling unit as in claim 23 wherein said temperature detector is a thermocouple.]

[25. A cooling unit as in claim 24 wherein said cryogenic container is a replaceable container.]

[26. A cooling unit as in claim 25 wherein said control means comprises a microprocessor for providing a controlled spray from said cryogenic container.]

[27. A cooling unit as in claim 26 wherein said cooling transmitting element comprises a sapphire plate and wherein said microprocessor is programmed to provide a controlled spray from said cryogen container onto said sapphire plate.]

[28. A cooling unit as in claim 27 wherein said cryogen is tetrafluoethan.]

*29. A method for cryogenically treating tissue below a skin surface, comprising:*

*placing a hand-held unit in contact with the skin surface;*

*cryogenically cooling the skin surface by contacting the skin surface with a material which has high thermal conductivity;*

*monitoring a temperature of either the material or the skin surface; and*

*controlling an amount of time the hand-held unit is in contact with the skin surface and an amount of cooling applied in order to cryogenically reach a desired temperature of the tissue at a desired depth below the skin surface, which is lower than a temperature before treatment, to promote lymphatic drainage by cold therapy.*

*30. The method of claim 29, wherein the temperature of the material is monitored.*

*31. The method of claim 29, wherein the temperature of the skin surface is monitored.*

*32. The method of claim 29, wherein the temperature is monitored with a thermocouple.*

*33. The method of claim 32, wherein the temperature of the skin surface is controlled so as to not fall below 0 degrees Centigrade for more than one second.*

*34. The method of claim 29, wherein the cooling results in skin rejuvenation.*

*35. The method of claim 29, wherein the amount of cooling applied is automatically controlled in response to the monitored temperature.*

*36. The method of claim 29, wherein the tissue below the skin surface is destroyed without any significant damage to the skin surface.*

*37. The method of claim 29, wherein the tissue comprises epidermal tissue.*

*38. The method of claim 29, wherein the material is cooled by evaporation of a cryogenic fluid.*

*39. The method of claim 29, wherein the cooling results in either removal of wrinkles or removal of spider veins.*

*40. The method of claim 29, wherein a temperature of all desired tissue layers being treated are controlled.*

*41. The method of claim 29, wherein cooling of the skin tissue is accompanied by no heating with laser light or other heating mechanism.*

*42. The method of claim 29, further comprising:*

*cleaning the skin surface with alcohol prior to placing the hand-held unit in contact with the skin.*

*43. The method of claim 29, further comprising:*

*heating the skin surface.*

*44. The method of claim 43, wherein the skin surface is heated prior to being cooled.*

*45. The method of claim 43, wherein the skin surface is heated as it is cooled.*

*46. The method of claim 29, wherein the material has a convex surface that contacts the skin surface.*

*47. The method of claim 29, wherein the material has a planar surface that contacts the skin surface.*

*48. The method of claim 29, wherein the cooling results in cryogenic treatment of skin surface lesions.*

*49. A method for cryogenically treating tissue below a skin surface, comprising:*

*placing a hand-held unit in contact with the skin surface;*

*cryogenically cooling the skin surface by contacting the skin surface with a material which has high thermal conductivity;*

*monitoring a temperature of either the material or the skin surface; and*

*controlling an amount of time the hand-held unit is in contact with the skin surface and an amount of cooling applied in order to cryogenically reach a desired temperature of the tissue at a desired depth below the skin surface, which is lower than a temperature before treatment, to promote lymphatic drainage by cold therapy,*

*wherein cooling of the skin tissue is accompanied by no heating with laser light or other heating mechanism.*

*50. The method of claim 49, wherein the temperature of the material is monitored.*

*51. The method of claim 49, wherein the temperature of the skin surface is monitored.*

*52. The method of claim 49, wherein the temperature is monitored with a thermocouple.*

*53. The method of claim 49, wherein the temperature of the skin surface is controlled so as to not fall below 0 degrees Centigrade for more than one second.*

*54. The method of claim 49, wherein the cooling results in skin rejuvenation.*

*55. The method of claim 49, wherein the amount of cooling applied is automatically controlled in response to the monitored temperature.*

*56. The method of claim 49, wherein the tissue below the skin surface is destroyed without any significant damage to the skin surface.*

*57. The method of claim 49, wherein the tissue comprises epidermal tissue.*

*58. The method of claim 49, wherein the material is cooled by evaporation of a cryogenic fluid.*

*59. The method of claim 49, wherein the cooling results in either removal of wrinkles or removal of spider veins.*

*60. The method of claim 49, wherein a temperature of all desired tissue layers being treated are controlled.*

*61. The method of claim 49, further comprising:*

*cleaning the skin surface with alcohol prior to placing the hand-held unit in contact with the skin.*

*62. The method of claim 49, further comprising:*

*heating the skin surface.*

*63. The method of claim 62, wherein the skin surface is heated prior to being cooled.*

*64. The method of claim 62, wherein the skin surface is heated as it is cooled.*

*65. The method of claim 49, wherein the material has a convex surface that contacts the skin surface.*

*66. The method of claim 49, wherein the material has a planar surface that contacts the skin surface.*

*67. The method of claim 49, wherein the cooling results in cryogenic treatment of skin surface lesions.*

* * * * *